United States Patent [19]

Hamanaka et al.

[11] Patent Number: 4,521,533

[45] Date of Patent: Jun. 4, 1985

[54] SALTS OF 6-ALPHA-(AMINOMETHYL)PENICILLANIC ACID 1,1-DIOXIDE ESTERS AND BETA-LACTAM ANTIBIOTICS

[75] Inventors: Ernest S. Hamanaka, Gales Ferry; John G. Stam, Waterford, both of Conn.

[73] Assignee: Pfizer Inc., New York, N.Y.

[21] Appl. No.: 630,147

[22] Filed: Jul. 12, 1984

[51] Int. Cl.³ .................. A61K 31/675; A61K 31/43; C07D 499/26
[52] U.S. Cl. ................................. 514/80; 260/239.1; 514/195; 514/196; 514/197; 514/198
[58] Field of Search ..................... 260/239.1; 424/271, 424/200

[56] References Cited

U.S. PATENT DOCUMENTS

| | | | |
|---|---|---|---|
| 3,699,096 | 10/1972 | Weissenburger | 260/239.1 |
| 4,309,347 | 1/1982 | Bigham | 260/245.2 R |
| 4,342,693 | 8/1982 | Sakamoto et al. | 549/229 |
| 4,446,144 | 5/1984 | Von Daehne | 424/270 |
| 4,452,796 | 6/1984 | Barth | 424/246 |

*Primary Examiner*—Natalie Trousof
*Assistant Examiner*—Vera C. Clarke
*Attorney, Agent, or Firm*—Charles J. Knuth; Albert E. Frost; James M. McManus

[57] ABSTRACT

Salts of readily hydrolyzable esters of 6-alpha-(aminomethyl)penicillanic acid 1,1-dioxide and (a) prodrug forms of ampicillin and amoxicillin or (b) ampicillin and amoxicillin and a dibasic acid are readily absorbed following oral adminstration, and are useful in treating bacterial infections.

16 Claims, No Drawings

SALTS OF 6-ALPHA-(AMINOMETHYL)PENICILLANIC ACID 1,1-DIOXIDE ESTERS AND BETA-LACTAM ANTIBIOTICS

BACKGROUND OF THE INVENTION

One of the most well-known and widely used class of antibacterial agents are the so-called beta-lactam antibiotics. These compounds are characterized in that they have a nucleus consisting of a 2-azetidinone (beta-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin and carbenicillin; typical examples of common cephalosporins are cephalothin, cephalexin and cefazolin.

However, despite the wide use and wide acceptance of the beta-lactam antibiotics as valuable chemotherapeutic agents, they suffer from the major drawback that certain members are not active against certain microorganisms. It is thought that in many instances this resistance of a particular microorganism to a given beta-lactam antibiotic results because the microorganism produces a beta-lactamase. The latter substances are enzymes which cleave the beta-lactam ring of penicillins and cephalosporins to give products which are devoid of antibacterial activity. However, certain substances have the ability to inhibit beta-lactamases, and when a beta-lactamase inhibitor is used in combination with a penicillin or cephalosporin it can increase or enhance the antibacterial effectiveness of the penicillin or cephalosporin against certain beta-lactamase producing microorganisms. It is considered that there is an enhancement of antibacterial effectiveness when the antibacterial activity of a combination of a beta-lactamase inhibiting substance and a beta-lactam antibiotic is significantly greater than the sum of the antibacterial activities of the individual components against beta-lactamase producing microorganisms.

The present invention relates to salts of 6-alpha-(aminomethyl)penicillanic acid 1,1-dioxide esters readily hydrolyzable in vivo and the prodrug 6-(4-phenyl-2,2-dimethyl-5-oxoimidazolidin-1-yl)penicillanic acid (hetacillin) and the prodrug 6-(4-p-hydroxyphenyl-2,2-dimethyl-5-oxoimidazolidin-1-yl)penicillanic acid.

The invention further relates to salt combinations of 6-alpha-(aminomethyl)penicillanic acid 1,1-dioxide esters readily hydrolyzable in vivo, ampicillin or amoxicillin and a dibasic acid.

These salts are especially useful in providing orally absorbable prodrug forms of 6-alpha-(aminomethyl)-penicillanic acid 1,1-dioxide and the appropriate beta-lactam antibiotic.

Pharmaceutical compositions comprising the above-mentioned salts as well as a method for increasing the oral effectiveness of certain beta-lactam antibiotics by the use of such salts are also part of the present invention.

Co-pending U.S. patent application Ser. No. 434,371, filed Oct. 21, 1982 discloses compounds of the formulae

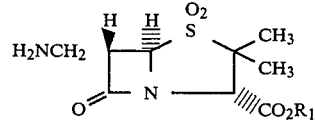

and

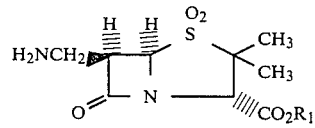

wherein $R_1$ is hydrogen or a conventional ester forming radical which is hydrolyzable under physiological conditions as beta-lactamase inhibitors useful in combination with active beta-lactam antibiotics.

Other compounds previously reported as beta-lactamase inhibitors useful in combination with beta-lactam antibiotics for the treatment of bacterial infections include penicillanic acid 1,1-dioxide and esters thereof readily hydrolyzable in vivo (Barth, U.S. Pat. No. 4,234,579); the bis-methanediol ester of sulbactam (Bigham, U.S. Pat. No. 4,309,347); various 6-beta-(hydroxymethyl)penicillanic acid 1,1-dioxides and esters thereof (Kellogg, U.S. Pat. No. 4,287,181); and 6-beta-(aminomethyl)penicillanic acid (McCombie, U.S. Pat. No. 4,237,051). Talampicillin (USAN generic name), the 1H-isobenzofuran-3-on-1-yl ester of ampicillin (Clayton et al., J. Med. Chem., 19, pp. 1385–1390, 1976), and (5-methyl-2-oxo-1,3-dioxolen-4-yl)methyl ester of ampicillin (Sakamoto et al., U.S. Pat. No. 4,342,693) exemplify those in vivo hydrolyzable ester radicals of particular interest in the present case. Above cited Clayton et al. also illustrates various crotonolactonyl and butyrolactonyl esters of ampicillin as in vivo hydrolyzable esters.

U.K. patent application No. 2,053,220, published Feb. 4, 1981, broadly discloses beta-lactamase inhibiting compounds of the formula

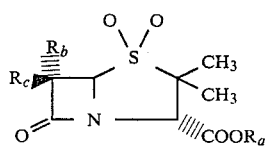

The definitions of $R_a$, $R_b$ and $R_c$ define literally an infinite number of compounds. These definitions, by appropriate selection of $R_a$, $R_b$ and $R_c$, may possibly define the 6-alpha-(aminomethyl)penicillanic acid 1,1-dioxides of present interest. No specific method for preparation of these compounds is present in the disclosure of this U.K. application, and there is no hint or suggestion that from among the infinity of compounds proposed, the present aminomethyl compounds are preferred compounds, possessing the particularly highly potent beta-lactamase inhibitory activity.

Recently, U.S. Pat. No. 4,446,144 disclosed salts between certain 6-beta-halopenicillanic acids and beta-lactam antibiotics or prodrug forms thereof.

SUMMARY OF THE INVENTION

The salts of this invention are of the formula

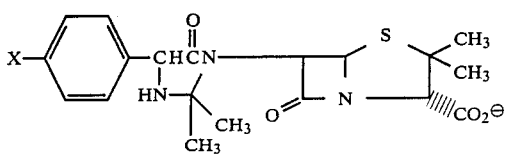

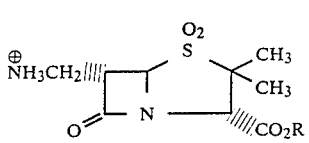

where X is hydrogen or hydroxy and R is an ester forming residue readily hydrolyzable in vivo.

Preferred are salts wherein the ester forming residue readily hydrolyzable in vivo is alkanoyloxymethyl of three to six carbon atoms, alkoxycarbonyloxymethyl of three to six carbon atoms, 1-(alkoxycarbonyloxy)ethyl of four to six carbon atoms, 3-phthalidyl, 4-crotonolactonyl or (5-methyl-2-oxo-1,3-dioxolen-4-yl)methyl.

Especially preferred are salts where X is hydrogen and R is pivaloyloxymethyl or ethoxycarbonyloxymethyl, and where X is hydroxy and R is pivaloyloxymethyl or ethoxycarbonyloxymethyl.

Also within the scope of the present invention are salts of the formula

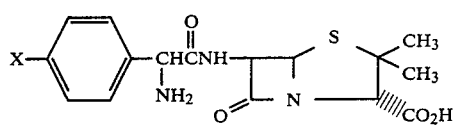

$R_1-SO_3H$

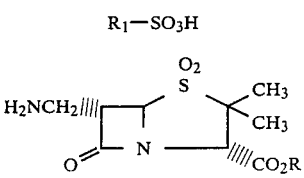

wherein X is hydrogen or hydroxy, R is an ester forming residue readily hydrolyzable in vivo and $R_1$ is hydroxy or $A-SO_3H$, $A-CO_2H$ or $A-PO_3H_2$ where A is alkylene of two to four carbon atoms, phenylene or cycloalkylene of five to six carbon atoms.

Preferred within this group of salts are those wherein the ester forming residue readily hydrolyzable in vivo is alkanoyloxymethyl of three to six carbon atoms, alkoxycarbonyloxymethyl of three to six carbon atoms, 1-(alkoxycarbonyloxy)ethyl of four to six carbon atoms, 3-phthalidyl, 4-crotonolactonyl or (5-methyl-2-oxo-1,3-dioxolen-4-yl)methyl.

Especially preferred are salts wherein X is hydrogen, R is pivaloyloxymethyl and $R_1$ is hydroxy or 3-sulfophenyl. Also especially preferred are salts wherein X is hydroxy, R is pivaloyloxymethyl and $R_1$ is 4-carboxyphenyl or hydroxy.

The present invention also relates to a pharmaceutical composition useful in treating bacterial infections comprising an antibacterially effective amount of the aforementioned salts and a pharmaceutically acceptable carrier.

In addition, the present invention also includes a method for treating a subject suffering from a bacterial infection which comprises administering to said subject an antibacterially effective amount of the aforementioned salts.

DETAILED DESCRIPTION OF THE INVENTION

The salts of the formula

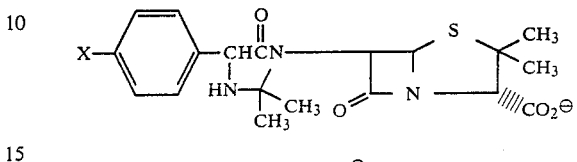

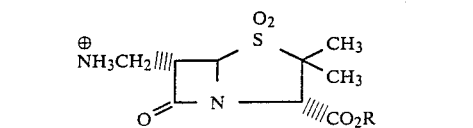

wherein X and R are previously defined are prepared by combining equimolar amounts of the appropriate prodrug of ampicillin or amoxicillin with the requisite 6-alpha-(aminomethyl)penicillin acid ester 1,1-dioxide free base in a suitable solvent and allowing the mixture or solution to stir at room temperature for as long as overnight, followed by removal of the solvent.

Suitable solvents which may be employed for the formation of these salts are those which do not alter the structures of the starting materials and solubilize each of the starting reagents to at least a moderate degree. Such solvents include tetrahydrofuran, chloroform, methylene chloride, toluene, benzene and ethyl acetate. The preferred solvent is methylene chloride.

Salts of the formula

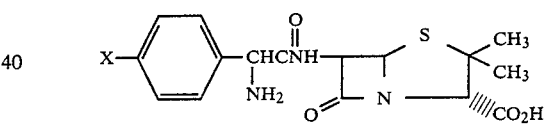

$R_1-SO_3H$

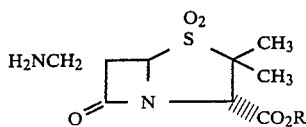

wherein X, R and $R_1$ are as previously defined, are prepared by contacting equimolar amounts of the ampicillin (X=H) or amoxicillin (X=OH) with the requisite dibasic acid, $R_1SO_3H$, and the appropriate ester of 6-alpha-(aminomethyl)penicillanic acid 1,1-dioxide in a suitable solvent and allowing the mixture or solution to stir at about 0° C. for ten to thirty minutes.

Suitable solvents for the formation of these salts are those which will not cause excessive degradation of any of the starting reagents, solubilize the reagents to an appreciable extent and are miscible with water. It is preferred that the solvent for contacting the starting reagents for these salts be composed of a water miscible organic solvent and water. It is preferred the organic solvent be tetrahydrofuran and that said solvent be combined with water 1:1(v:v).

After the reagents have stirred in the cold for the requisite period of time, the organic solvent is removed in vacuo, the residual water extracted with a water immiscible solvent, such as ethyl acetate, and the aqueous layer lyophilized to give the desired salt.

The reagents for preparing these salts are readily available or can be prepared by procedures known and familiar to those skilled in the art; the preparation of esters of 6-alpha-(aminomethyl)penicillanic acid 1,1-dioxide are described herein.

As previously indicated, the salts of the present invention are especially useful in combatting bacterial infections, and are readily absorbed when administered orally.

The beta-lactam antibiotic component of the salts derived from 6-(4-phenyl- and 4-p-hydroxyphenyl-2,2-dimethyl-5-oxoimidazolidin-1-yl)penicillanic acids are, on absorption, readily hydrolyzed to ampicillin and amoxicillin. The component of the salts derived from esters of 6-alpha-(aminomethyl)penicillanic acid 1,1-dioxide are also readily hydrolyzed in vivo to provide compounds, wherein R is hydrogen, which are potent inhibitors of beta-lactamase.

When using a salt of the present invention it is administered preferably in formulation with standard pharmaceutical carriers or diluents. A pharmaceutical composition comprising a pharmaceutically-acceptable carrier and a salt of the present invention will normally contain from about 5 to about 80 percent of the pharmaceutically acceptable carrier by weight.

When using the salts of the present invention, the prescribing physician will ultimately decide the dosage to be used in a human subject. In general, the daily oral dosage of the salts of the present invention will normally be in the range of from about 25 mg to about 400 mg per kilogram of body weight. These figures are illustrative only, however, and situations may exist where dosages outside this range may be required.

The present invention is illustrated by the following examples, although it should be understood that the invention is not limited to the specific details of these examples.

Nuclear magnetic resonance spectra (NMR) were measured at 60 MHz for solutions in deuterochloroform ($CDCl_3$), perdeutero dimethyl sulfoxide (DMSO-$d_6$) or deuterium oxide ($D_2O$) or as noted otherwise, and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet.

EXAMPLE 1

Salt of Hetacillin and Pivaloyloxymethyl 6-alpha-aminomethylpenicillanate 1,1-dioxide To a solution of 1.2 g. of sodium bicarbonate in 15 ml. of water and 100 ml. of methylene chloride cooled to 0° C. is added 3.03 g. (0.006 mole) of pivaloyloxymethyl 6-alpha-aminomethylpenicillanate 1,1-dioxide p-tosylate salt over a ten minute period with stirring. The methylene chloride layer is separated and the aqueous layer extracted with 20 ml. of fresh methylene chloride. The combined methylene chloride extracts are dried over sodium sulfate and the drying agent filtered. The filtrate comprised of pivaloyloxymethyl 6-alpha-(aminomethyl)penicillanate 1,1-dioxide in 120 ml. of methylene chloride is treated with 2.33 g (0.006 mole) of hetacillin [J. Org. Chem., 31, 899 (1966)]. The resulting suspension is allowed to stir at room temperature overnight, and is then concentrated to give the desired salt.

EXAMPLE 2

Salt of 6-(4-p-Hydroxyphenyl-2,2-dimethyl-5-oxoimidazolidin-1-yl)penicillanic acid (X=OH) and Pivaloyloxymethyl 6-alpha-(aminomethyl)penicillanate 1,1-dioxide Following the procedure of Example 1, and using 6-(4-p-hydroxyphenyl-2,2-dimethyl-5-oxoimidazolidin-1-yl)penicillanic acid [J. Chem. Soc., C (10) 1920 (1971)] in place of hetacillin, the desired salt is obtained.

EXAMPLE 3

The procedure of Example 1 is employed, starting with the appropriate ester of 6-alpha-(aminomethyl)-penicillanic acid 1,1-dioxide and hetacillin or 6-(4-p-hydroxyphenyl-2,2-dimethyl-5-oxoimidazolidin-1-yl) penicillanic acid, to give the following salts:

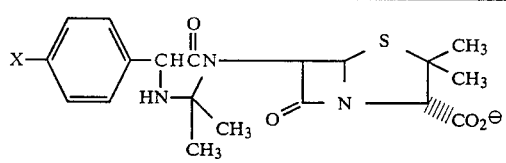

| X | R |
|---|---|
| H | $CH_2OCOCH_3$ |
| H | $CH_2OCOC_2H_5$ |
| H | $CH_2OCOCH(CH_3)_2$ |
| H | $CH_2OCO_2CH_3$ |
| H | $CH_2OCO_2C_2H_5$ |
| H | $CH_2OCO_2CH(CH_3)_2$ |
| H | $CH(CH_3)OCO_2C_2H_5$ |
| H | $CH(CH_3)OCO_2CH(CH_3)_2$ |
| H | 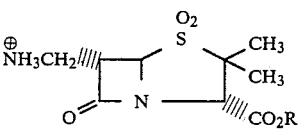 |
| H | $-CH_2C{=}{=}CCH_3$ with O—C(=O)—O bridge 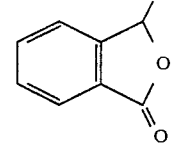 |
| H | 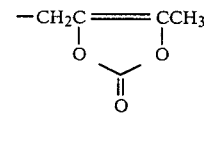 |
| OH | $CH_2OCOCH_3$ |
| OH | $CH_2OCOCH(CH_3)_2$ |
| OH | $CH_2OCO_2C_2H_5$ |
| OH | $CH_2OCO_2CH(CH_3)_2$ |
| OH | $CH(CH_3)OCO_2C_2H_5$ |

| | -continued |
|---|---|
| OH | CH(CH₃)OCO₂CH(CH₃)₂ |
| OH | 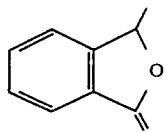 |
| OH | 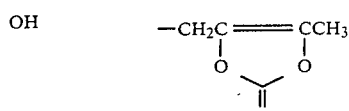 |
| OH | 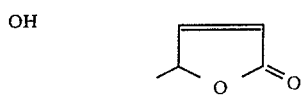 |

EXAMPLE 4

Sulfate Salt of 6-(D-Alpha-amino-p-hydroxyphenylacetamido)penicillanic Acid and Pivaloyloxymethyl 6-alpha-aminomethylpenicillanate 1,1-dioxide To 50 ml. of tetrahydrofuran-water (1:1, v:v) containing 1.89 g. (0.0045 mole) of 6-(D-alpha-amino-p-hydroxyphenylacetamido)penicillanic acid trihydrate and 4.5 ml. of 1M sulfuric acid and cooled to 0° C. is added 1.5 g. (0.0045 mole) of pivaloyloxymethyl 6-alpha-aminomethylpenicillanate 1,1-dioxide. The resulting solution is stirred at 0° C. for ten minutes and the tetrahydrofuran removed in vacuo. The aqueous layer is lyophilized to give the desired salt.

EXAMPLE 5

Sulfate Salt of 6-(D-Alpha-amino-phenylacetamido)penicillanic Acid and Pivaloyloxymethyl 6-alpha-aminomethylpenicillanate 1,1-dioxide Using the procedure of Example 4, and employing 6-(D-alpha-amino-phenylacetamido)penicillanic acid trihydrate and pivaloyloxymethyl 6-alpha-(aminomethyl)penicillanate 1,1-dioxide the titled salt is obtained.

EXAMPLE 6

Employing the procedure of Example 4, and starting with 6-(D-alpha-amino-p-hydroxyphenylacetamido)-penicillanic acid trihydrate or 6-(D-alpha-amino-(phenylacetamido)penicillanic acid trihydrate, the appropriate ester of 6-alpha-(aminomethyl)penicillanic acid 1,1-dioxide and sulfuric acid, the following salts are prepared:

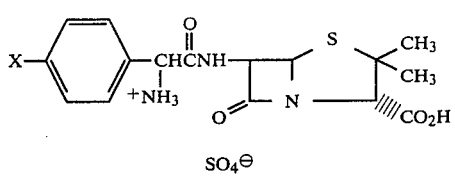

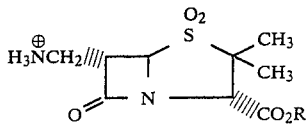

| X | R |
|---|---|
| H | CH₂OCOCH₃ |
| H | CH₂OCOC₂H₅ |
| H | CH₂OCOCH(CH₃)₂ |
| H | CH₂OCO₂CH₃ |
| H | CH₂OCO₂C₂H₅ |
| H | CH₂OCO₂CH(CH₃)₂ |
| H | CH(CH₃)OCO₂C₂H₅ |
| H | CH(CH₃)OCO₂CH(CH₃)₂ |
| H | 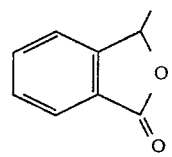 |
| H | 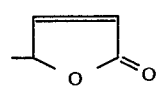 |
| H | 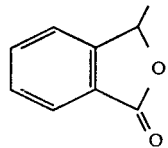 |
| OH | CH₂OCOCH₃ |
| OH | CH₂OCOCH(CH₃) |
| OH | CH₂OCO₂C₂H₅ |
| OH | CH₂OCO₂CH(CH₃)₂ |
| OH | CH(CH₃)OCO₂C₂H₅ |
| OH | CH(CH₃)OCO₂CH(CH₃)₂ |
| OH | 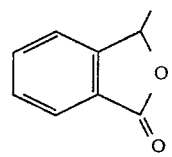 |
| OH | 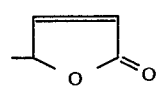 |
| OH |  |

EXAMPLE 7

Benzene Disulfonic Acid Salt of 6-(D-alpha-amino-p-hydroxyphenylacetamido)penicillanic acid and Pivaloyloxymethyl 6-alpha-(aminomethyl)penicillanate 1,1-dioxide To 2 g. (0.0048 mole) of 6-(D-alpha-amino-p-hydroxyphenylacetamido)penicillanic acid trihydrate and 1.36 g. (0.0048 mole) of 1,3-benzenedisulfonic acid hydrate in 60 ml. of tetrahydrofuran-water (1:1, v:v) cooled to 0° C. is added 1.6 g. (0.0048 mole) of pivaloyloxymethyl 6-alpha-(aminomethyl)penicillanate 1,1-dioxide in 5 ml.

of tetrahydrofuran, and the resulting solution allowed to stir for fifteen minutes. The tetrahydrofuran is removed under vacuum and the aqueous residue extracted with ethyl acetate (2×50 ml.). The aqueous layer is lyophilized to give the desired salt.

EXAMPLE 8

Benzene Disulfonic Acid Salt of 6-(D-alpha-aminophenylacetamido)penicillanic Acid and Pivaloyloxymethyl 6-alpha-(aminomethyl)penicillanate 1,1-dioxide To 2.01 g. (0.005 mole) of 6-(D-alpha-aminophenylacetamido)penicillanic acid trihydrate and 1.41 g. (0.005 mole) of 1,3-benzenedisulfonic acid hydrate in 50 ml. of tetrahydrofuran-water (1:1, v:v) cooled to 0° C. is added 1.66 g. (0.005 mole) of pivaloyloxymethyl 6-alpha-(aminomethyl)penicillanate 1,1-dioxide. After stirring for fifteen minutes the tetrahydrofuran is removed in vacuo and the residual aqueous solution extracted with ethyl acetate. The aqueous layer is separated and lyophilized to give the desired salt.

EXAMPLE 9

Starting with amoxicillin or ampicillin trihydrate, an appropriate ester of 6-alpha-(aminomethyl) penicillanic acid 1,1-dioxide and a dibasic acid, and repeating the procedure of Example 7, the following salts are prepared:

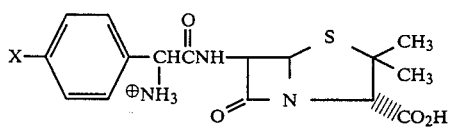

$R_1\text{---}SO_3^=$

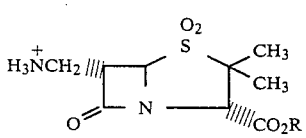

| X | $R_1$* | R |
|---|---|---|
| H | 1,3-$C_6H_4SO_3H$ | $CH_2OCOCH_3$ |
| H | 1,4-$C_6H_4SO_3H$ | $CH_2OCOC_2H_5$ |
| H | 1,3-$C_6H_4CO_2H$ | $CH_2OCOC(CH_3)_3$ |
| H | 1,4-$C_6H_4CO_2H$ | $CH_2OCOCH(CH_3)_2$ |
| H | 1,3-$C_6H_4PO_3H_2$ | $CH_2OCOC_2H_5$ |
| H | —$CH_2CH_2SO_3H$ | $CH_2OCOC(CH_3)_3$ |
| H | —$CH_2CH_2CH_2CO_2H$ | $CH_2OCOCH_3$ |
| H | —$CH_2CH(CH_3)CH_2PO_3H_2$ | $CH_2OCOC_2H_5$ |
| H | 1,4-cyclo $C_6H_{10}SO_3H$ | $CH_2OCOCH(CH_3)_2$ |
| H | 1,3-$C_6H_4SO_3H$ | $CH_2OCO_2C_2H_5$ |
| H | 1,3-$C_6H_4CO_2H$ | $CH_2OCO_2CH(CH_3)_2$ |
| H | 1,3-$C_6H_4PO_3H_2$ | $CH_2OCO_2CH_3$ |
| H | —$CH_2CH_2SO_3H$ | $CH_2OCO_2C_2H_5$ |
| H | —$CH_2CH(CH_3)CH_2PO_3H_2$ | $CH_2OCO_2C_2H_5$ |
| H | 1,4-cyclo $C_6H_{10}SO_3H$ | $CH_2OCO_2C_2H_5$ |
| H | 1,3-$C_6H_4SO_3H$ | 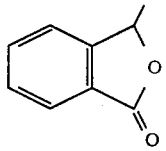 |
| H | 1,4-$C_6H_4CO_2H$ | —CH$_2$C=CCH$_3$ with O, O, C=O |
| H | —$CH_2CH_2SO_3H$ | —CH$_2$C=CCH$_3$ with O, O, C=O |
| H | 1,3-$C_6H_4PO_3H_2$ | (butyrolactone-like ring) |
| OH | 1,3-$C_6H_4SO_3H$ | $CH_2OCOCH_3$ |
| OH | 1,3-$C_6H_4CO_2H$ | $CH_2OCOCH(CH_3)_2$ |
| OH | 1,3-$C_6H_4PO_3H_2$ | $CH_2OCOC(CH_3)_3$ |
| OH | $CH_2CH_2SO_3H$ | $CH_2OCO_2C_2H_5$ |
| OH | 1,4-cyclo $C_6H_{10}SO_3H$ | $CH_2OCOCH_3$ |
| OH | 1,4-$C_6H_4SO_3H$ | $CH_2OCO_2CH_3$ |
| OH | 1,3-$C_6H_4CO_2H$ | $CH_2OCO_2C_2H_5$ |
| OH | $CH_2CH_2SO_3H$ | $CH_2OCO_2CH(CH_3)_2$ |
| OH | —$CH_2CH(CH_3)CH_2PO_3H_2$ | $CH_2OCO_2C_2H_5$ |
| OH | 1,3-$C_6H_4SO_3H$ | —CH$_2$C=CCH$_3$ with O, O, C=O |
| OH | 1,3-$C_6H_4CO_2H$ | (isopropylphthalide-like) |
| OH | $CH_2CH_2SO_3H$ | (butyrolactone-like ring) |

*Depicted in unionized form.

PREPARATION A

Pivaloyoxymethyl 6-alpha-(aminomethyl)penicillanate 1,1-dioxide p-Tosylate Salt

A1. Benzyl 6-alpha-bromo-6-beta-(benzyloxycarbonylaminomethyl)penicillanate and 6-beta-bromo-6-alpha-(benzyloxycarbonylaminomethyl)penicillanate To a solution of benzyl 6,6-dibromopenicillanate (108.73 g, 0.242 mole) in 600 ml dry tetrahydrofuran (THF), cooled to −78° C., was added an ether solution of methyl magnesium bromide (83.5 ml of 2.9M). After stirring for 15 minutes at −78° a solution of benzyloxycarboxamidomethyl acetate (27 g, 0.121 mole) in 200 ml dry THF was added over 10 minutes. After stirring for an hour at −78° the reaction was quenched by the addition of 14.52 ml of acetic acid. The mixture was warmed to room temperature and volatiles removed in vacuo at less than 35° C. Ethyl acetate was added to dissolve the residue, and the solution washed with water (100 ml), aqueous NaHCO$_3$ (100 ml), and 2×100 ml water, then dried over Na$_2$SO$_4$ and concentrated in vacuo to 113 g of oily product. The oil was column chromatographed on 1.2 kg silica gel, eluting first with 6 liters of 1:1 hexane:chloroform and then with chloroform. The first 6 liters of eluate was discarded. Further eluate was collected in 25 ml fractions. Fraction numbers 181–190 were concentrated. The pnmr spectrum of the residue in CDCl$_3$ revealed benzyl 6-alpha-bromo-6-beta-(benzyloxycarbonylaminomethyl)penicillanate: delta/TMS 1.37 (3H, s), 1.57 (3H, s), 3.86 (2H, d, J=6Hz), 4.42 (1H, s), 5.06 (2H, s), 5.12 (2H, s), 5.52 (1H, s), 7.25 (10H, s). Fraction numbers 201–249 were concentrated and the pnmr spectrum of this residue in CDCl$_3$ revealed benzyl 6-beta-bromo-6-alpha-(benzyloxycarbonylaminomethyl)penicillanate: delta/TMS 1.36 (3H, s), 1.60 (3H, s), 3.90 (2H, d, J=6.2Hz), 4.47 (1H, s), 5.07 (2H, s), 5.14 (2H, s), 5.40 (1H, t, J=6.2), 5.47 (1H, s), 7.28 (5H, s), 7.30 (5H, s). The product from fraction numbers 171–240 was combined and concentrated to 22 g of foam and used in the experiment of Preparation A2.

A2. Benzyl 6-beta-(Benzyloxycarbonylaminomethyl)penicillanate

To a solution of title products (epimeric mixture) of the preceding Preparation A1 (22 g, 0.0413 mole) in 100 ml benzene was added tri-n-butyltin hydride (32.7 ml, 0.124 mole). The mixture was refluxed under N$_2$ for 2 hours, concentrated in vacuo to an oil and the oil triturated 4×100 ml hexane. The residual viscous oil was taken up in 70 ml of ether, from which title product crystallized over 1 hour [8.1 g in two crops] pnmr/CDCl$_3$/delta/TMS: 1.37 (3H, s), 1.57 (3H, s), 3.58 (3H, m), 4.34 (1H, s), 5.04 (2H, s), 5.12 (2H, s), 5.33 (1H, d, J=4Hz), 7.32 (10H, s).

Benzyl 6-alpha-(benzyloxycarbonylaminomethyl)penicillanate is recovered by concentration of mother liquors and chromatography.

A3. Benzyl 6-beta-(Benzyloxycarbonylaminomethyl)penicillanate 1,1-Dioxide

To a solution of benzyl 6-beta-(benzyloxycarbonylaminomethyl)penicillanate of Preparation A2 (8.0 g, 0.0176 mole) in 200 ml ethyl acetate cooled to 0°–5° C. was added m-chloroperbenzoic acid (10.68 g, 0.0528 mole). The mixture was warmed to room temperature, stirred for 6 hours, recooled to 0°–5° C. and diluted with 50 ml of saturated NaHSO$_3$. The organic layer was separated, washed 2×50 ml saturated NaHCO$_3$ and 2×50 ml H$_2$O, dried over Na$_2$SO$_4$ and concentrated in vacuo to a viscous oil (8.6 g). The oil was chromatographed on 250 g silica gel, eluting with 19:1 CHCl$_3$:ethyl acetate in 25 ml fractions. Fractions 44–150 were combined and concentrated in vacuo to yield title product as a white gummy foam [7.6 g; pnmr/CDCl$_3$/delta/TMS 1.25 (3H, s), 1.49 (3H, s), 3.98 (3H, m), 4.45 (1H, s), 4.59 (1H, d, J=4Hz), 5.09 (2H, s), 5.19 (2H, q), 5.36 (1H, br), 7.36 (10H, s)].

A4. Benzyl 6-alpha-(Benzyloxycarbonylaminomethyl)penicillanate 1,1-Dioxide

To a solution of benzyl 6-beta-(benzyloxycarbonylaminomethyl)penicillanate 1,1-dioxide (3.3 g., 6.79 mmoles) in 100 ml. of chloroform was added 1,5-diazabicyclo[4.3.0]non-5-ene (DBN, 0.607 g., 4.9 mmoles). The mixture was stirred at room temperature for 15 minutes, diluted with 50 ml. 1N HCL, and the layers separated. The organic layer was washed 2×50 ml. H$_2$O, dried over Na$_2$SO$_4$ and concentrated in vacuo to an oil (3.1 g.). The oil was column chromatographed on
150 g. silica gel, eluting with 1:9 ethyl acetate: CHCl$_3$ in 20 ml. fractions. Fractions 26–37 were combined and concentrated in vacuo to yield purified title product, as a viscous oil which crystallized on standing [1.9 g.; mp 112°–113° C.; pnmr/CDCl$_3$/delta/TMS 1.20 (3H, s), 1.49 (3H, s), 3.65 (3H, m), 4.32 (1H, s), 4.59 (1H, m), 5.07 (2H, s), 5.14 (2H, q), 5.30 (1H, br), 7.32 (10H, s)].

A5. 6-alpha-(Benzyloxycarbonylaminomethyl)penicillanic Acid 1,1-Dioxide

Benzyl 6-alpha-(benzyloxycarbonylaminomethyl)penicillanate 1,1-dioxide (11.2 g) in THF (70 ml) and H$_2$O (50 ml) in the presence of 6 g 10% Pd/C was partially hydrogenated at 50 psig for 30 minutes. Catalyst was removed by filtration over a pad of diatomaceous earth, THF was distilled from the filtrate in vacuo, and the aqueous residue was extracted with 100 ml ethyl acetate. The organic layer was separated, dried (Na$_2$SO$_4$) and evaporated to yield title product as a foam, 3.0 g; pnmr/CDCl$_3$/TMS 1.40 (3H, s), 1.55 (3H, s), 3.70 (3H, m), 4.31 (1H, s), 4.58 (1H, m), 5.04 (2H, s), 7.24 (5H, s).

The aqueous layer was concentrated to yield crystalline 6-alpha-(aminomethyl)penicillanic acid 1,1-dioxide, 3.1 g.

A6. Pivaloyloxymethyl 6-alpha-(Benzyloxycarbonylaminomethyl)penicillanate 1,1-Dioxide The title product of the preceding Example (6.75 g, 17 mmoles) and N,N-diisopropylethylamine (3.34 ml, 18.7 mmoles) were dissolved in dimethylformamide (50 ml), chloromethyl pivalate (2.72 ml, 18.7 mmoles) were added, and the mixture allowed to stir at ambient temperature for 20 hours. The reaction mixture was diluted with ethyl ether (300 ml), washed with water (2×100 ml), dried (Na$_2$SO$_4$) and evaporated in vacuo to an oil. The oil was dissolved in 100 ml ether, washed 3×50 ml H$_2$O, dried (Na$_2$SO$_4$) and concentrated in vacuo to yield purified title product as a viscous oil, 4.4 g, pnmr/CDCl$_3$/TMS 1.20 (9H, s), 1.34 (3H, s), 1.51 (3H, s), 3.64 (3H, m), 4.31 (1H, s), 4.60 (1H, d), 5.04 (2H, s), 5.71 (2H, q), 7.24 (5H, s).

A7. p-Toluenesulfonate Salt of Pivaloyloxymethyl 6-alpha-(Aminomethyl)penicillanate 1,1-Dioxide Title product of the preceding Example (1.8 g, 3.53 mmoles) was hydrogenated in a mixture of THF (40 ml) and H$_2$O (20 ml) over 1.8 g of 10% Pd/C in the presence of pyridinium p-toluenesulfonate (1.77 g, 7.06 mmoles) at 50 psig for 1.5 hours. The catalyst was recovered by filtration over diatomaceous earth and the filtrate stripped of THF in vacuo, during which the title product crystallized, 1.2 g, mp 214°–215° C. (dec.); pnmr/DMSO-d$_6$/TMS 1.16 (9H, s), 1.32 (3H, s), 1.48 (3H, s), 2.28 (3H, s), 3.34 (2H, m), 3.82 (1H, m), 4.60 (1H, s), 5.14 (1H, d, J=2Hz), 5.75 (2H, ABq), 7.23 (4H, ABq).

Anal. Calcd. for C$_{15}$H$_{24}$O$_7$N$_2$S.C$_7$H$_7$SO$_3$H: C, 48.16; H, 5.88; N, 5.11. Found: C, 48.31; H, 6.11; N, 5.08.

PREPARATION B

B1.

Starting with 6-alpha-(benzyloxycarbonylaminomethyl)penicillanic acid 1,1-dioxide (Preparation A5) and the appropriate alkanoyloxymethyl-, alkoxycarbonyloxymethyl-, 1-(alkoxycarbonyloxy)ethyl- or 4-crotonolactonyl halide, and employing the procedure of Preparation A6, the following intermediate esters are prepared:

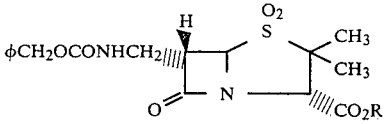

| R |
|---|
| $CH_2OCOCH_3$ |
| $CH_2OCOC_2H_5$ |
| $CH_2OCOCH(CH_3)_2$ |
| $CH_2OCO_2CH_3$ |
| $CH_2OCO_2C_2H_5$ |
| $CH_2OCO_2CH(CH_3)_2$ |
| $CH(CH_3)OCO_2C_2H_5$ |
| $CH(CH_3)OCO_2CH(CH_3)_2$ |

B2.

Employing the intermediate esters of Preparation B1 and using the procedure of Preparation A7, the p-toluenesulfonate salt of the following esters are prepared:

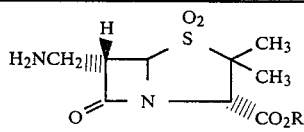

| R |
|---|
| $CH_2OCOCH_3$ |
| $CH_2OCOC_2H_5$ |
| $CH_2OCOCH(CH_3)_2$ |
| $CH_2OCO_2CH_3$ |
| $CH_2OCO_2C_2H_5$ |
| $CH_2OCO_2CH(CH_3)_2$ |
| $CH(CH_3)OCO_2C_2H_5$ |
| $CH(CH_3)OCO_2CH(CH_3)_2$ |

PREPARATION C (5-Methyl-2-oxo-1,3-dioxolen-4-yl)methyl 6-alpha-(aminomethyl)penicillanate 1,1-dioxide p-toluenesulfonate salt

C1. Tetrabutylammonium 6-alpha-(Aminomethyl)penicillanate 1,1-Dioxide

To a solution of 6-alpha-(aminomethyl)penicillanic acid 1,1-dioxide (0.524 g, 2.0 mmoles) in 50 ml chloroform was added tetrabutylammonium hydroxide (1.3 ml of 1.527N, 2.0 mmoles). After stirring 5 minutes, the organic layer was separated, dried and evaporated to yield title product as an oil, 0.806 g.

Alternatively, to 15.7 g (0.06 moles) of the same starting material in 450 ml methylene chloride at 0°–5° C. was added 39.3 ml (0.06 moles) of the same hydroxide over 5 minutes. The cooling bath was removed and after stirring 5 minutes, title product (30.2 g) isolated according to the method of the preceding paragraph.

C2. Tetrabutylammonium 6-alpha-[(2-methoxycarbonyl-1-methylvinyl)aminomethyl]penicillanate 1,1-Dioxide Title product of Preparation C1 (0.806 g) was dissolved in 1 ml methyl acetoacetate and heated at 60° for 15 minutes under nitrogen. The mixture was cooled, diluted with 75 ml benzene and concentrated in vacuo to yield title product, all of which was used directly in the next step.

Alternatively, title product of Preparation C1 (30.2 g, about 0.06 moles) was combined with 30 ml of methyl acetoacetate and stirred for 5 minutes at room temperature. Benzene (150 ml) was added and the mixture stripped in vacuo to an oil, a step which was twice repeated. The resulting oil was triturated 3 times with 200 ml portions of hexane, decanting each time with final drying of the oil under high vacuum. The yield of title product was 36.06 g.

C3. (5-Methyl-2-oxo-1,3-dioxolen-4-yl)methyl 6-alpha-[(2-Methoxycarbonyl-1-methylvinyl)aminomethyl]penicillanate 1,1-Dioxide The entire batch of title product prepared according to the first paragraph of Preparation C2 in 20 ml of acetone was added to a solution of (5-methyl-2-oxo-1,3-dioxolen-4-yl)methyl bromide (0.772 g., 4.0 mmoles) in 10 ml of acetone. After stirring 0.5 hour, the reaction mixture was concentrated to an oil, dissolved in chloroform and filtered through 30 g silica gel with chloroform eluant. Fractions of 30 ml were collected—fractions 3–6 on evaporation gave title product as a foam, 0.38 g; tlc $R_f$ 0.2 (7:3 $CHCl_3$:ethyl acetate).

C4. (5-Methyl-2-oxo-1,3-dioxolen-4-yl)methyl 6-alpha-(Aminomethyl)penicillanate 1,1-Dioxide p-Toluenesulfonate Title product of Preparation C3 (0.38 g, 0.807 mmole) was dissolved in 20 ml of water saturated ethyl acetate. p-Toluenesulfonic acid monohydrate (0.153 g, 0.807 mmole) in 10 ml ethyl acetate was added dropwise over 5 minutes. After stirring 0.5 hour under nitrogen, the mixture was concentrated to an oil, 0.53 g, which crystallized from chloroform, 0.22 g; pnmr/DMSO-$d_6$/TMS/delta (ppm): 1.34 (3H, s), 1.51 (3H, s), 2.17 (3H, s), 2.31 (3H, s), 3.40 (2H, m), 3.94 (1H, m), 4.53 (1H, s), 5.13 (3H, m), 7.30 (4H, q), 8.03 (3H, br. s).

PREPARATION D

1H-Isobenzofuran-3-on-1-yl 6-alpha-(aminomethyl)penicillanate 1,1-dioxide p-toluenesulfonate salt

D1. 1H-Isobenzofuran-3-on-1-yl 6-alpha-[(2-methoxycarbonyl-1-methylvinyl)aminomethyl]penicillanate 1,1-Dioxide By the procedures of Preparations C1 and C2, 6-alpha-(aminomethyl)penicillanic acid 1,1-dioxide (2.62 g) was converted to Preparation C2 title product, 4.3 g, as an oil. The latter was dissolved in 50 ml acetone and mixed with 1H-isobenzofuran-3-on-1-yl bromide (3-bromophthalide) (1.52 g, 7.15 mmoles) in 20 ml acetone. After stirring 2 hours, the mixture was concentrated and the residue triturated to yield crude product as an oil, 4.3 g. The latter was filtered on 60 g silica gel, eluting with 300 ml chloroform. The eluant was concentrated to yield title product as a foam, 0.8 g; tlc $R_f$ 0.5 (9:1 chloroform:ethyl acetate).

D2. 1H-Isobenzofuran-3-on-1-yl 6-alpha-(Aminomethyl)penicillanate 1,1-Dioxide p-Toluenesulfonate By the procedure of Preparation 4, title product of the preceding Preparation D1 (0.8 g, 1.62 mmoles) was converted to present title product, initially isolated as a foam. The foam was triturated with 100 ml of diethyl ether and scratched to solidfy, 0.69 g; pnmr/CDCl$_3$/TMS/delta (ppm): 1.40 (3H, s), 1.58 (3H, s), 1.95 (3H, s), 2.21 (3H, s), 3.60 (3H, s), 3.73 (3H, m), 4.40 (2H, m), 4.52 (1H, s), 5.00 (2H, s).

We claim:

1. Salts of the formula

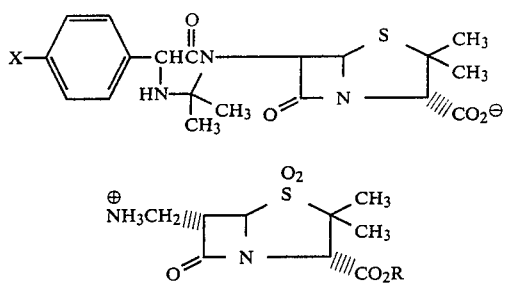

wherein X is selected from the group consisting of hydrogen and hydroxy, and R is an ester forming residue readily hydrolyzable in vivo.

2. A salt of claim 1, wherein ester forming residues readily hydrolyzable in vivo are selected from the group consisting of alkanoyloxymethyl having from three to six carbon atoms, alkoxycarbonyloxymethyl having from three to six carbon atoms, 1-(alkoxycarbonyloxy)ethyl having from four to six carbon atoms, 3-phthalidyl, 4-crotonolactonyl and (5-methyl-2-oxo-1,3-dioxolen-4-yl)methyl.

3. The salt of claim 2, wherein X is hydrogen and R is pivaloyloxymethyl.

4. The salt of claim 2, wherein X is hydroxy and R is pivaloyloxymethyl.

5. The salt of claim 2, wherein X is hydrogen and R is ethoxycarbonyloxymethyl.

6. The salt of claim 2, wherein X is hydroxy and R is ethoxycarbonyloxymethyl.

7. Salts of the formula

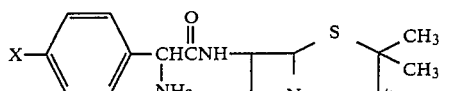

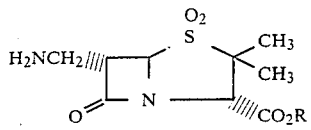

wherein X is selected from the group consisting of hydrogen and hydroxy, R is an ester forming residue readily hydrolyzable in vivo; and R$_1$ is selected from the group consisting of hydroxy, and A—SO$_3$H, A—CO$_2$H and A—PO$_3$H$_2$ where A is selected from the group consisting of alkylene having two to four carbon atoms, phenylene and cycloalkylene having from five to six carbon atoms.

8. A salt of claim 7, wherein ester forming residues readily hydrolyzable in vivo are selected from the group consising of alkanoyloxymethyl having from three to six carbon atoms, alkoxycarbonyloxymethyl having from three to six carbon atoms, 1-(alkoxycarbonyloxy)ethyl having from four to six carbon atoms, 3-phthalidyl, 4-crotonolactonyl and (5-methyl-2-oxo-1,3-dioxolen-4-yl)methyl.

9. A salt of claim 8, wherein X is hydrogen and R is pivaloyloxymethyl.

10. The salt of claim 9, wherein R$_1$ is hydroxy.

11. The salt of claim 9, wherein R$_1$ is 3-sulfophenyl.

12. A salt of claim 8, wherein X is hydroxy and R is pivaloyloxymethyl.

13. The salt of claim 12, wherein R$_1$ is 4-carboxyphenyl.

14. The salt of claim 12, wherein R$_1$ is hydroxy.

15. A pharmaceutical composition in dosage unit form for treating infectious bacterial diseases which comprises an antibacterially effective amount of a salt according to claim 1 or 7 and a pharmaceutically acceptable carrier therefor.

16. A method of treating a subject suffering from a bacterial infection which comprises administering to said subject an antibacterially effective amount of a salt according to claim 1 or 7.

* * * * *